(12) United States Patent
Frick (10) Patent No.: US 7,765,114 B2
(45) Date of Patent: Jul. 27, 2010

(54) PATIENT TREATMENT MANAGEMENT METHOD USING TREATMENT REGIMENS

(75) Inventor: W. Vaughn Frick, Bloomfield Hills, MI (US)

(73) Assignee: Ashbec, LLC, Bloomfield Hills, MI (US)

( * ) Notice: Subject to any disclaimer, the term of this patent is extended or adjusted under 35 U.S.C. 154(b) by 0 days.

(21) Appl. No.: 11/947,357

(22) Filed: Nov. 29, 2007

(65) Prior Publication Data

US 2008/0065424 A1    Mar. 13, 2008

Related U.S. Application Data

(63) Continuation of application No. 11/356,384, filed on Feb. 16, 2006, now abandoned.

(60) Provisional application No. 60/692,627, filed on Jun. 21, 2005.

(51) Int. Cl.
G06F 19/00 (2006.01)
(52) U.S. Cl. .................. 705/3; 705/2; 600/300
(58) Field of Classification Search .............. 705/2, 705/3, 4; 600/300
See application file for complete search history.

(56) References Cited

U.S. PATENT DOCUMENTS

| | | | |
|---|---|---|---|
| 4,839,806 A | 6/1989 | Goldfischer et al. |
| 4,857,716 A | 8/1989 | Gombrich et al. |
| 4,916,441 A | 4/1990 | Gombrich |
| 5,416,695 A | 5/1995 | Stutman et al. |
| 5,625,334 A | 4/1997 | Compton |
| 5,781,442 A | 7/1998 | Engleson et al. |
| 5,822,544 A | 10/1998 | Chaco et al. |
| 5,911,687 A | 6/1999 | Sato et al. |
| 5,912,818 A | 6/1999 | McGrady et al. |

(Continued)

FOREIGN PATENT DOCUMENTS

GB        2301685 A      12/1996

OTHER PUBLICATIONS

Koppel, "What do we know about medication errors made via a CPOE system versus those made via handwritten orders?", Critical Care, Aug. 22, 2005, pp. 427-428, http://ccforum.com/content/9/5/427, University of Pennsylvania, USA.

(Continued)

*Primary Examiner*—R. D Rines
(74) *Attorney, Agent, or Firm*—Fraser Clemens; Martin & Miller LLC; William J. Clemens (57) ABSTRACT

A system and a method for managing patient treatment stores in the database a patient history for each patient including data related to observations, test results, diagnoses, treatment regimen(s) and a treatment plan associated with the patient. The treatment plan is administered to the patient and medical device operating data related to the tasks of the associated treatment regimen is stored in the database. A reminder is issued if a task associated with the treatment regimen is not completed on time and the effectiveness of the treatment regimen is evaluated based upon the data stored in the database so that only effective treatment regimens are retained in the system. The system performs treatment planning, treatment monitoring, hospital monitoring, healthcare insurance billing, patient billing, research and analysis support, supply chain management and personnel scheduling.

16 Claims, 6 Drawing Sheets

U.S. PATENT DOCUMENTS

| | | | |
|---|---|---|---|
| 6,039,251 | A | 3/2000 | Holowko et al. |
| 6,070,761 | A | 6/2000 | Bloom et al. |
| 6,122,351 | A | 9/2000 | Schlueter, Jr. et al. |
| 6,397,190 | B1 | 5/2002 | Goetz |
| 6,401,072 | B1 * | 6/2002 | Haudenschild et al. ......... 705/3 |
| 6,480,745 | B2 | 11/2002 | Nelson et al. |
| 6,671,563 | B1 | 12/2003 | Engelson et al. |
| 6,731,989 | B2 | 5/2004 | Engleson et al. |
| 6,790,198 | B1 | 9/2004 | White et al. |
| 6,804,656 | B1 | 10/2004 | Rosenfeld et al. |
| 6,822,554 | B2 | 11/2004 | Vrijens et al. |
| 6,830,180 | B2 | 12/2004 | Walsh |
| 6,834,203 | B2 | 12/2004 | Bardy |
| 6,915,170 | B2 | 7/2005 | Engleson et al. |
| 6,985,870 | B2 | 1/2006 | Martucci et al. |
| 7,107,106 | B2 | 9/2006 | Engleson et al. |
| 7,117,041 | B2 | 10/2006 | Engleson et al. |
| 7,233,228 | B2 | 6/2007 | Lintell |
| 7,251,311 | B2 | 7/2007 | Tsunezumi |
| 7,379,885 | B1 * | 5/2008 | Zakim ........................... 705/2 |
| 2001/0050610 | A1 | 12/2001 | Gelston |
| 2001/0051787 | A1 * | 12/2001 | Haller et al. .................. 604/66 |
| 2002/0169636 | A1 | 11/2002 | Eggers et al. |
| 2002/0196141 | A1 | 12/2002 | Boone et al. |
| 2003/0009244 | A1 | 1/2003 | Engleson et al. |
| 2003/0036683 | A1 * | 2/2003 | Kehr et al. .................. 600/300 |
| 2003/0141981 | A1 | 7/2003 | Bui et al. |
| 2004/0078231 | A1 * | 4/2004 | Wilkes et al. .................. 705/2 |
| 2004/0104271 | A1 | 6/2004 | Martucci et al. |
| 2004/0172299 | A1 | 9/2004 | Paul |
| 2004/0183683 | A1 | 9/2004 | Funahashi |
| 2004/0193325 | A1 | 9/2004 | Bonderud et al. |
| 2005/0038669 | A1 * | 2/2005 | Sachdeva et al. ............... 705/2 |
| 2005/0102167 | A1 | 5/2005 | Kapoor |
| 2005/0119914 | A1 | 6/2005 | Batch |
| 2005/0215867 | A1 | 9/2005 | Grigsby et al. |
| 2006/0047538 | A1 * | 3/2006 | Condurso et al. .............. 705/3 |

OTHER PUBLICATIONS

Han et al., "Unexpected Increased Mortality After Implementation of a Commercially Sold Computerized Physician Order Entry System", Pediatrics Journal, Dec. 2005, vol. 116, No. 6, pp. 1506-1512, American Academy of Pediatrics, USA.

Walsh, et al., "Medication Errors Related to Computerized Order Entry for Children", Pediatrics Journal, Nov. 2006, vol. 118, No. 5, pp. 1872-1879, American Academy of Pediatrics, USA.

Wears et al., "Computer Technology and Clinical Work: Still Waiting for Godot" JAMA, Mar. 9, 2005, vol. 293, No. 10, pp. 1261-1263, American Medical Association, USA.

Garg et al., "Effects of Computerized Clinical Decision Support Systems on Practitioner Performance and Patient Outcomes: A Systematic Review" JAMA, Mar. 9, 2005, vol. 293, No. 10, pp. 1223-1238, American Medical Association, USA.

Littlejohns et al., "Evaluating computerised health information systems: hard lessons still to be learnt" BMJ, Apr. 19, 2003, vol. 326, pp. 860-863, BMJ Publishing Group Ltd., GB.

Kaplan et al., "Health IT Success and Failure: Recommendations from Literature and an AMIA Workshop", Journal of the American Medical Informatics Association, vol. 16, No. 3, May/Jun. 2009, pp. 291-299, American Medical Information Association, USA.

Jha et al., "Use of Electronic Health Records in U.S. Hospitals", The New England Journal of Medicine, Apr. 16, 2009, vol. 360, No. 16, pp. 1628-1638, Massachusetts Medical Society, USA.

Kuperman et al., "Using Commercial Knowledge Bases for Clinical Decision Support: Opportunities, Hurdles, and Recommendations", Journal of the American Medical Informatics Association, vol. 13, No. 4, Jul./Aug. 2006, pp. 369-371, American Medical Information Association, USA.

* cited by examiner

PATIENT TREATMENT MANAGEMENT METHOD USING TREATMENT REGIMENS

CROSS-REFERENCE TO RELATED APPLICATION

The application is a continuation of U.S. Ser. No. 11/356,384 filed Feb. 16, 2006, which in turn claims the benefit of U.S. provisional patent application Ser. No. 60/692,627 filed Jun. 21, 2005.

BACKGROUND OF THE INVENTION

The present invention relates generally to an apparatus and a method for managing the treatment of hospital patients.

The U.S. Pat. No. 4,839,806 discloses a computerized dispensing of medication that provides automated direction and guidance for nurses and allows for data entry regarding whether or not medication was dispensed (See Abstract).

The U.S. Pat. No. 4,857,716 discloses a patient identification and verification system and method that include an overdue drug alert system (Col. 16, lines 28-50) in conjunction with a patient data entry and recording system. The system also includes checks for drug incompatibility (Col. 14, lines 40-43).

The U.S. Pat. No. 4,916,441 discloses a portable handheld terminal 22 having a display screen 40 and a bar code reader 42 that is contemplated for use as the point of care data input and retrieval device in a patient care system and in communication with a network file server 24 via a local area network. Scheduled actions, defined by a customized hospital parameter table, may be displayed on the display screen along with a warning light and/or an audible beep. (Col. 11, lines 60-67). A "scratch-pad" capability (Col. 12, lines 12-30) is also provided for the terminal, but is recited to be stored in the terminal only.

The U.S. Pat. No. 5,416,695 discloses a method and apparatus for alerting patients and medical personnel of emergency medical situations. An exemplary embodiment of the apparatus is recited for use with an ambulatory patient 300 and provides body function data from sensors 320 via a telemetry device 310 to a host computer 12. The host computer provides alerts if any of the body function data exceeds limits set by a physician or other caregiver.

The U.S. Pat. No. 5,822,544 discloses a patient care and communication system featuring audio, visual, and data communication (See Abstract).

The U.S. Pat. No. 5,912,818 discloses a system for tracking and dispensing medical items that includes a plurality of hook registers 10 that are adapted to contain medical devices, medications, or the like. The hook registers are in communication with a computer 84 via a local area network 82, which is also in communication with an administrator's workstation 86, an electronic lock drawer 96, a hospital information system 90, an admission-discharge-transfer system 88, and a medical dispenser 100. The system discusses the use of alarms (Col. 22, lines 28-35).

The U.S. Pat. No. 6,039,251 discloses a method and system for secure control of a medical device such as a pump 26 at a patient's home 11 from a medical care facility 12.

The U.S. Pat. No. 6,070,761 discloses a vial loading method and apparatus for intelligent admixture and delivery of intravenous drugs that includes communication with nursing stations, data entry terminals, and patient databases by a hospital network (See FIG. 17).

The U.S. Pat. No. 6,397,190 discloses a veterinary medication monitoring system and apparatus that utilizes a PDA and alarm functions for a veterinary treatment system, where the PDA receives data at the veterinarian's office and the PDA provides alarms to the handler/owner of the animal to provide care. Actions taken are also stored in the PDA.

The U.S. Pat. No. 6,790,198 discloses a patient medication IV delivery pump with wireless communication to a hospital information management system.

The U.S. Patent Application No. 2001/0050610 discloses a hospital informatics system that includes a plurality of interconnected modules (chart 200, clinical data entry 400, nursing functions 500, clinical guide 600, MD functions 700, kardex and pharmacy 800, admitting 900, order entry 1000, and administration 1100—See FIG. 1 and cover page).

The U.S. Patent Application No. 2002/0169636 discloses a system and method for managing patient care that includes a plurality of functional modules 16, 18, 20, and 22 in communication with a control unit 14 that controls of a patient care device 12 that is in turn in communication with a pharmacy system 34. The functional modules are recited to be a variety of pumps, monitors, or input/output devices (see Paragraph 26). Various databases (See FIG. 3) are utilized to provide operational protocols or characteristics for the modules 16, 18, 20, and 22.

The U.S. Patent Application No. 2003/0009244, 2004/0073329, and 2004/0143459 each disclose a patient care management system 30 and method for collecting data and managing patient care that includes a connection with a pharmacy information system 20 and a hospital information system 40 via a hospital network 5 as well as connections with a bedside CPU 80 and at least one infusion pump 92.

The U.S. Patent Application No. 2003/0141981 discloses a system and method for operating medical devices, such as an infusion pump 120, wherein a caregiver 116 utilizes a digital assistant 118 to control the infusion pump. The operation of the infusion pump is also modified by operating parameters entered by a treating physician (FIG. 5B) and confirmed by patient IDs such as on a wristband 112a and by a computer at a pharmacy 104. Alarms and errors are generated upon conflicts.

The U.S. Patent Application Nos. 2003/0135388 and 2004/0104271 disclose a medication delivery system for electronically controlling a medication delivery device 30 that includes a handheld computing device 22 that reads data from a patient tag 24 and medical container 28 before allowing the device to deliver medication through a catheter 37. The system contemplates preventing the activation of the delivery device if allergies, etc. are present (See FIG. 39).

The U.S. Patent Application No. 2004/0172299 discloses a system and method for facilitating clinical care that allows users to document numerous types of clinical interventions including patient assessment 12, problem identification 143, recommendations 16, outcome/follow-up 18, and status 20 (Paragraph 28 and FIG. 2).

The U.S. Patent Application No. 2004/0193325 discloses a method and apparatus to prevent medication error in a networked infusion system having an infusion device 20 and a computing device 26 connected by a network 30 that may be wired or wireless. An alerting device 28 is provided to notify medical personnel when the medication or the dose is not clinically acceptable.

SUMMARY OF THE INVENTION

The present invention concerns a patient treatment management system comprising: at least one network; at least one hospital information database in communication said at least one network; at least one treatment database in communication with said at least one network; and at least one handheld device in communication with said at least one network, said handheld device operable to transmit patient information to said hospital information database and said treatment database and receive patient care instructions from said treatment database.

The patient treatment management system according to the present invention comprises: at least one network; a treatment management system database in communication said at least one network; and at least one module in communication with said management system database through said at least one network, said at least one module being one of a treatment planning module; a treatment monitoring module; a hospital performance monitoring module; a healthcare insurance billing module; a patient billing module; a research and analysis module; a supply chain management module; and a personnel scheduling module.

A patient treatment management system for a hospital according to the present invention comprises: at least one database for storing data related to a patient including observations, test results, diagnosis and treatment regimen; at least one healthcare provider terminal for use by healthcare providers to exchange said data with said database; at least one monitoring device for sending medical device operating data related to the patient during the treatment regimen to said database; and a computer connected to said at least one database, said at least one healthcare provider terminal and said at least one monitoring device and generating an evaluation of the treatment regimen based upon said data. The system also can include at least one visual control connected to said computer for communicating to the healthcare providers information related to a potential problem associated with the treatment regimen. The system further can include at least one administration terminal connected to said computer for use by administrators to select and monitor performance measures of the treatment regimen. The system includes a software program operated by said computer and having at least one of a treatment planning module, a treatment monitoring module, a hospital monitoring module, a healthcare insurance billing module, a patient billing module, a research and analysis support module, a supply chain management module and a personnel scheduling module.

A method for managing patient treatment according to the present invention comprises the steps of: providing a database; storing in the database standard treatment regimens indexed by diagnosis and applicable to a wide variety of patients; storing in the database data related to patients including observations, test results, diagnoses and treatment regimens; storing in the database a patient specific treatment plan based on set treatment regimens (possibly customized); storing in the database medical device operating data related to the treatment regimens; storing in the database the results of executing the treatment plan to date including any adverse outcomes; and evaluating effectiveness of the treatment regimens based upon the data stored in the database. The method includes determining a diagnosis for a patient based upon the stored observations and test results data, identifying all of the stored treatment regimens associated with the diagnosis, either customizing one of the identified treatment regimens or creating a new treatment regimen, and storing in the database the customized treatment regimen or the new treatment regiment. The selected treatment regimen(s) will be combined if necessary and assigned as a treatment plan for a specific patient. The plan will be compared with the patient's known history to determine if there are identifiable incompatibilities. The method includes monitoring the administration of the treatment plan and issuing a reminder if a task associated with the treatment regimen is not completed on time. The method further includes monitoring the administration of the treatment plan, issuing an alert if a success indicator associated with the treatment regimen is not achieved and identifying other patients undergoing the same treatment regimen. The method also can include monitoring the selected performance measures associated with the treatment regimens.

The method can include generating visual controls to enable healthcare providers to anticipate and/or react to problems associated with administration of the treatment plans. The method also can include evaluating the treatment regimens and storing in the database only those treatment regimens that are effective. The system further can include using the data in the database to perform at least one of treatment planning, treatment monitoring, hospital monitoring, healthcare insurance billing, patient billing, research and analysis support, supply chain management and personnel scheduling.

DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENTS

U.S. provisional patent application Ser. No. 60/692,627 filed Jun. 21, 2005 is hereby incorporated herein by reference.

1.0 System Overview

Figure 1:
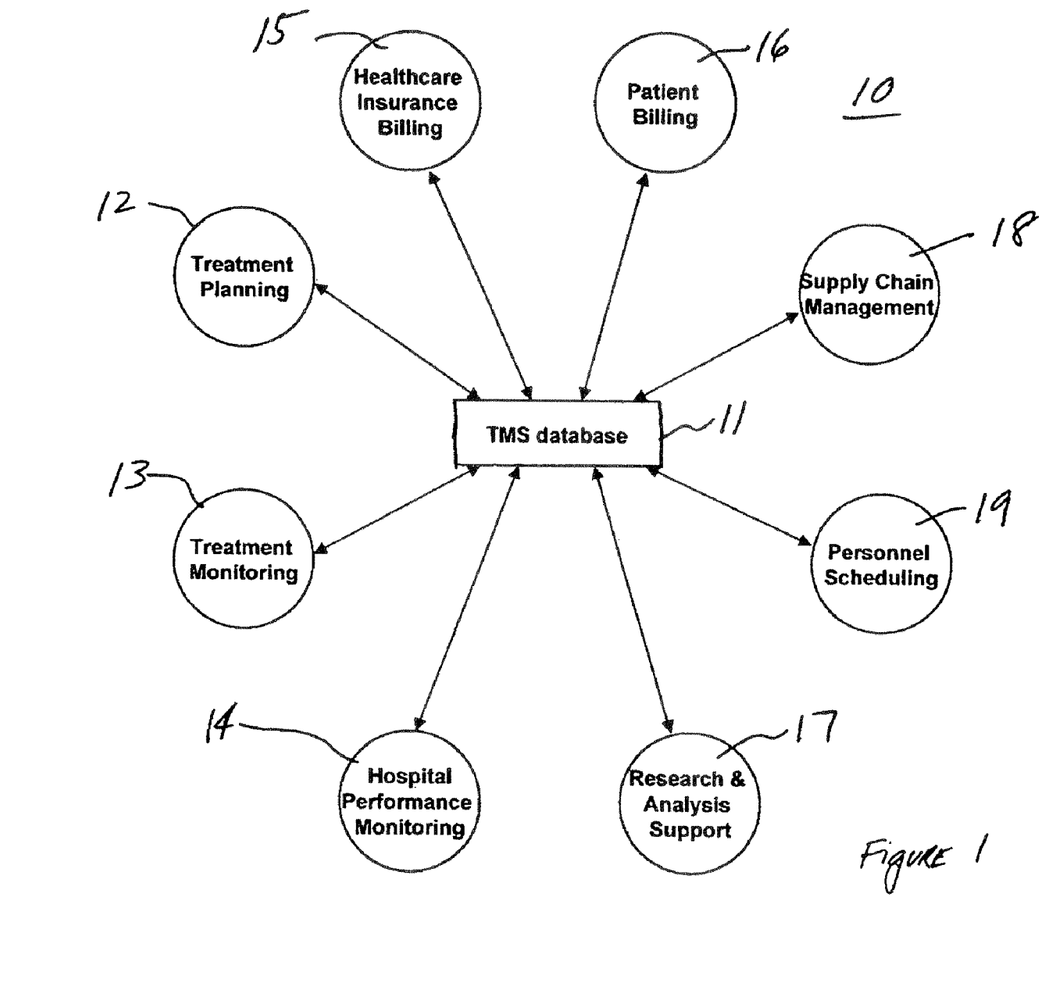
FIG. 1 is a block diagram of the treatment management system in accordance with the present invention.

A medical treatment management system (TMS) 10 in accordance with the present invention is shown in FIG. 1. A TMS database 11 is at the center of a plurality of modules that communicate information required by the system 10. The overall purpose of the TMS is to improve quality and lower the cost of inpatient hospital care. The TMS is designed to impact patient care immediately and capture information that can be used to analyze past events and improve future performance.

The modules that communicate with the TMS database 11 are:

Treatment Planning module 12

Treatment Monitoring module 13

Hospital Performance Monitoring module 14

Healthcare Insurance Billing module 15

Patient Billing module 16

Research & Analysis Support module 17

Supply Chain Management module 18

Personnel Scheduling module 19

2.0 Treatment Planning 2.1 The Treatment Planning module 12 draws on treatment regimens indexed by diagnosis in the TMS database 11. A treatment regimen may include a variety of "treatment events" such as:

- medications delivered in specific doses in specific intervals,
- physical therapy activities to manipulate a patient manually,
- surgical procedures,
- recurring events that capture information such as dietary requirements,
- a wide variety of tests and images used to determine the patient's condition and reaction to treatment.

The treatment regimen is a collection of these events that occur in sequence and possibly at specific time intervals. It is intended to include everything the hospital must do to treat a patient. Treatment sequence may be dependent on other treatments. For example, a specific test may be required at a certain time interval after a specific medication is administered or a particular surgical procedure is performed. For treatments other than tests or other activities whose sole function is information gathering, specific success criteria will be defined as well as known indicators that the treatment is not working. These criteria could be measurable results or more subjective in nature (i.e., "the patient should be experiencing less pain within one hour of taking this medication.").

When the treatment regimen is to be applied to a specific patient, the regimen will be compared to all information known about the patient (e.g., existing medications, allergies, etc.) to identify any unsuitable aspects of the treatment regimen for this particular patient. This includes functions such as those provided by traditional CPOE systems that support prescribing medications. It is also intended to include issues such as ambulatory limitations, allergies to food or other items that might be encountered in a hospital environment (e.g., latex), etc.

Figure 2:
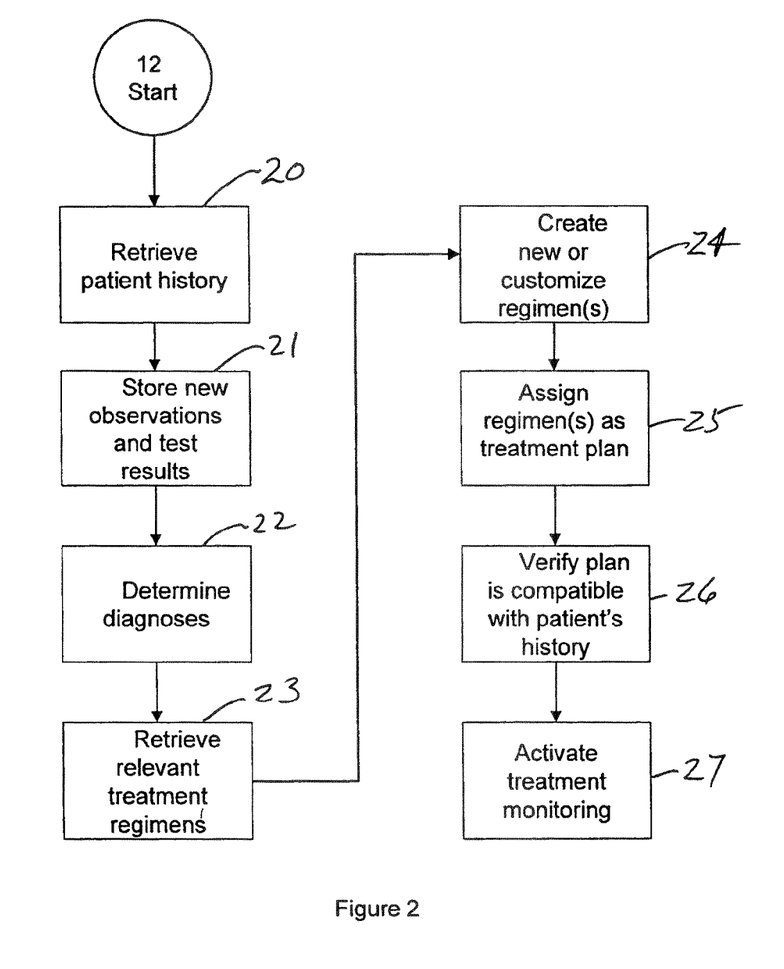
FIG. 2 is flow diagram of the operation of the treatment planning module shown in FIG. 1.

As a physician initially examines a patient, observations and test results are captured in the patient's history. As shown in FIG. 2, the treatment planning module 12 begins with a step 20 of retrieving the patient history from the TMS database 11. In a step 21, new observations and test results are stored in the patient history in the database. When the physician settles on a diagnosis in a step 22, the system can be used to identify alternative treatment regimens for the given diagnosis wherein all treatment regimens relevant to the diagnosis are retrieved from the database in a step 22. The physician can create a new treatment regimen or customize an existing treatment regimen in a step 24. The physician then assigns one or more treatment regimens as the treatment plan for the patient in a step 25. The system compares the treatment plan with the information in the patient history in a step 26 to verify that the plan is compatible with the history. In the simple case of diagnosing a single condition, the physician can accept a standard treatment program, customize an existing treatment regimen or create an entirely new treatment regimen in a step 24. If the physician chooses to customize or create a treatment regimen, that regimen can be saved for future use by that physician. Hospital administration will have the ability to allow access to these new treatment regimens by all physicians at the hospital. After the plan verification, treatment monitoring is activated in a step 27.

2.2 Physician has Ultimate Responsibility and Control

The system will assist in merging treatments for compound diagnoses but THE DOCTOR ALWAYS HAS ULTIMATE RESPONSIBILITY for ensuring that the treatment plan will be safe and effective. In the more complex case of treating one patient with multiple conditions, the physician will select a treatment regimen for each diagnostic code. The system will then create a preliminary treatment regimen for the specific patient by combining these treatment regimens. To the extent possible, the system will check for interactions between the combined treatment events and flag any questionable interactions. It will be the physician's responsibility to review the resulting treatment regimen and customize it as necessary to ensure the proper treatment regimen is ordered for this patient. Again, the physician will have the ability to save any customized treatment regimens so they never have to perform the same customization twice.

Figure 3:
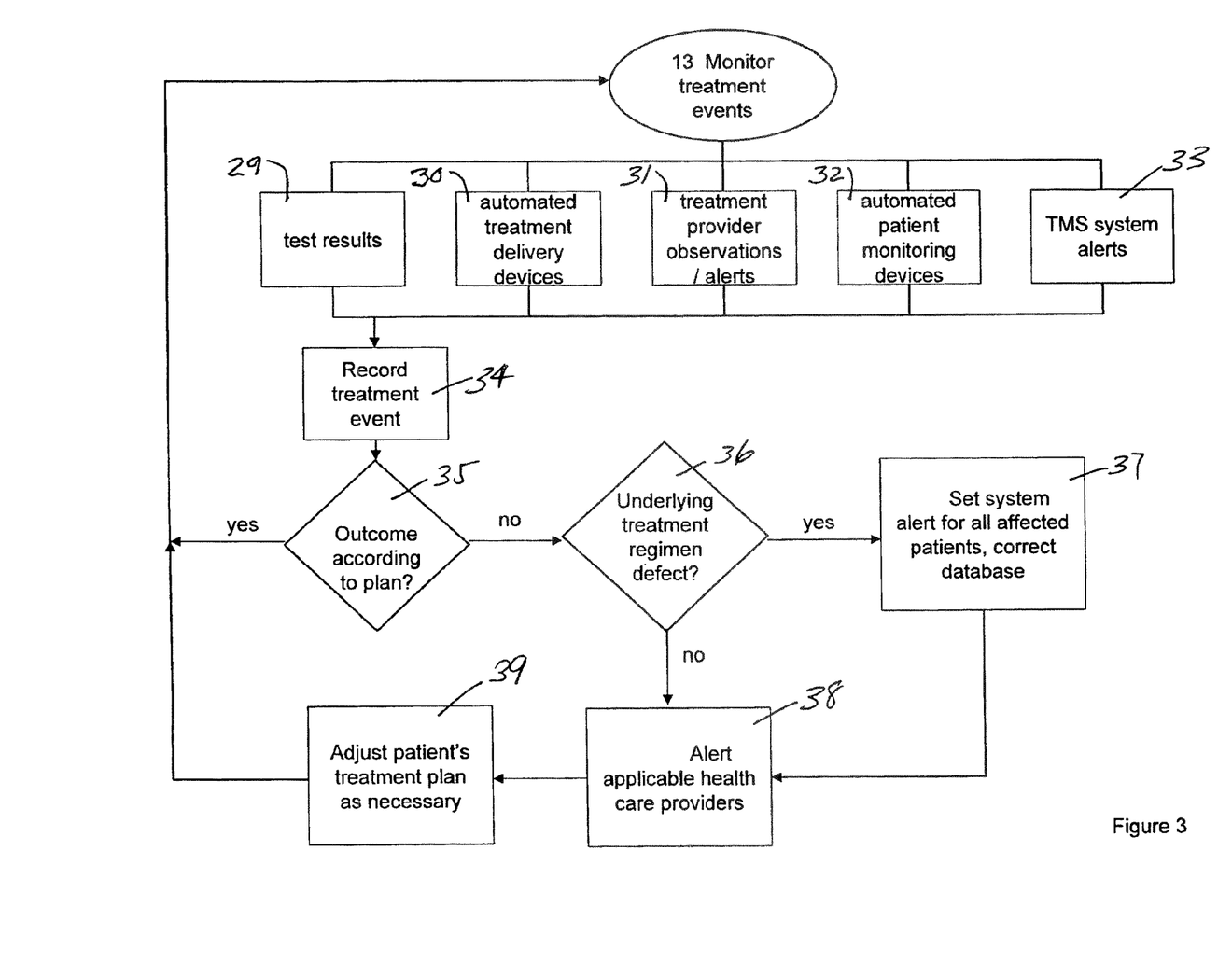
FIG. 3 is flow diagram of the operation of the treatment monitoring module shown in FIG. 1.

3.0 Treatment Monitoring 3.1 Monitors the Execution of the Physician-Approved Treatment Plan The Treatment Monitoring module 13 of the system 10 will monitor the patient's treatment for events as shown in FIG. 3. Such events include test results in a step 29, automated treatment delivery services in a step 30, treatment provider observations/alerts in a step 31, automated patient monitoring devices in a step 32, and TMS system alerts in a step 33. All of the events generated in the steps 29 through 33 are recorded in the database in a step 34. At a decision point 35, each event is checked as it occurs to determine whether the outcome is according to the treatment plan. If the outcome is according to plan, the method branches at "yes" and returns to the monitoring for the next event to occur or that has occurred. If the outcome is not according to plan, the method branches at "no" to a decision point 36. The decision point 36 determines whether there is an underlying regiment defect causing the outcome. If there is a defect, the method branches at "yes" to a step 37 wherein a system alert is set for all affected patients and the treatment regimen is corrected in the database. If there is no defect, the method branches at "no" to a step 38 wherein an alert is issued to the applicable healthcare providers. Next, the method executes a step 39 wherein the patient's treatment plan is adjusted as necessary and returns to the monitoring for the next event to occur or that has occurred.

The steps 36 through 39, for example, may deal with a task required by the treatment regimen that was not delivered in a timely fashion. The system will remind the healthcare provider responsible for completion of the task in the step 38. The system will continue to monitor the delivery of the treatment regimen and if the task is still not completed, an escalation process will begin. In the case of a treatment that is inconsistent with the treatment regimen, e.g. an incorrect medication dosage from an infusion pump, the responsible health care provider will be immediately notified with an alert. Escalation of notices for treatments inconsistent with the treatment regimen will be very rapid.

Success/failure indicators for specific treatments will have a default behavior as follows. If a specified success indicator does not occur, a low priority alert will be delivered to the attending nurse and will be delivered to the attending physician during the physician's next review of the patient record. The treatment regimen can require a higher priority alert for specific success/failure indications. For example, the occurrence of the indicator might trigger immediate paging of the physician and a high priority alert for the attending nurse or other hospital staff. These alerts can be customized during the creation of the treatment regimen database and further customized when the regimen is applied to a specific patient.

3.2 Monitors the Patient for Unexpected Responses to the Treatment

As described above, each treatment regimen will include the definition of indications that the treatment is working as expected. For example, the patient's temperature may be expected to lower by a certain amount in a certain timeframe. The average clotting time for a patient receiving a blood thinner might be expected to follow a predictable progression, etc. The patient's condition might be provided by patient monitoring equipment, test results or healthcare provider observations. In the event that the patient is not responding to the treatment as expected, the appropriate health care providers will be notified as specified in the treatment regimen. Information sources that will provide success/failure indicators could include staff interviews of the patient, continuous monitoring equipment linked to the hospital wireless area network (see below), lab results entered for the patient, or radiologist interpretation of imaging results.

There will of course be indicators of treatment success, failure or complications that are not anticipated in the treatment regimen. Any person that is responsible for delivering any portion of the treatment can raise an alert based on their judgment and observation of the patient's condition. The default system action will be to issue a high priority alert to the attending nurse, nursing supervisor, doctor on call and the patient's primary physician. However, the priority levels of the alerts in the default action can be customized by the hospital administration. The hospital administration can also add specific administrators that should be alerted in the event that problems are identified in a standard treatment regimen. The action taken in a specific case can also be customized by the person raising the alert. Regardless of any customization, at a minimum an alert will be delivered to the individuals mentioned above at some level of priority. The intent is not only to provide immediate assistance to the patient question but to quickly identify problems with standard treatment regimens before the problems can proliferate to additional patients.

When a problem is identified in a standard treatment regimen, the attending physician will have the ability to identify all of his or her additional patients that are being treated with that treatment regimen or a customized regimen based on the standard treatment regimen in a step 37. Hospital administration will have the same ability across the entire hospital. This will ensure that the standard treatment regimens will quickly improve and that the improvements will immediately be propagated to all affected patients. In effect, this will be a key mechanism used to facilitate the hospital's transformation to a learning organization.

3.3 Inputs from Healthcare Professionals Linked to Wireless Area Networks

Doctors, nurses and other health-care providers will access the system through portable devices that allow two-way communication with the system. At a minimum, this communication will be through one or more wireless area networks within the hospital. It may also include appropriately secure access through the Internet. Examples of the type of devices that might be suitable would include:
- Laptops (possibly using speech recognition)
- Tablet PC's
- PDA's (potentially with bar-code readers)
- Small, portable PC's that project keyboards and monitor displays onto any flat surface All portable or shared input devices should have the capability of using biometrics to identify the user of the device quickly and easily. One such example might be a fingerprint reader incorporated into the device. Non-portable devices used for input that do not have equivalent functionality should be connected to a security system that identifies the (one) individual given access to the secure area containing the device. The security system must be capable of detecting both the entry and exit of the authorized user and any other potential users. If any potential unauthorized users have entered the secure area, the device connection will be treated as not secure regardless of the presence of an authorized user.

3.4 Inputs from Automated Devices

Health care providers will be responsible for creating the link between an automated device and the patient. For example, when a nurse connects the patient's IV to an infusion pump that is connected to the wireless area network, he or she will identify the patient attached to the device for the system. This may be done by bar-code scanning of a patient bracelet, reading an RFID tag on the patient or some similar technology. If the device is turned off, the link will be broken. Examples of such automated devices might be:
- imaging systems
- infusion pumps or other treatment delivery systems
- a wide variety of patient monitoring devices

4.0 Hospital Performance Monitoring

4.1 Performance Measures for Hospital Administration

Figure 4:
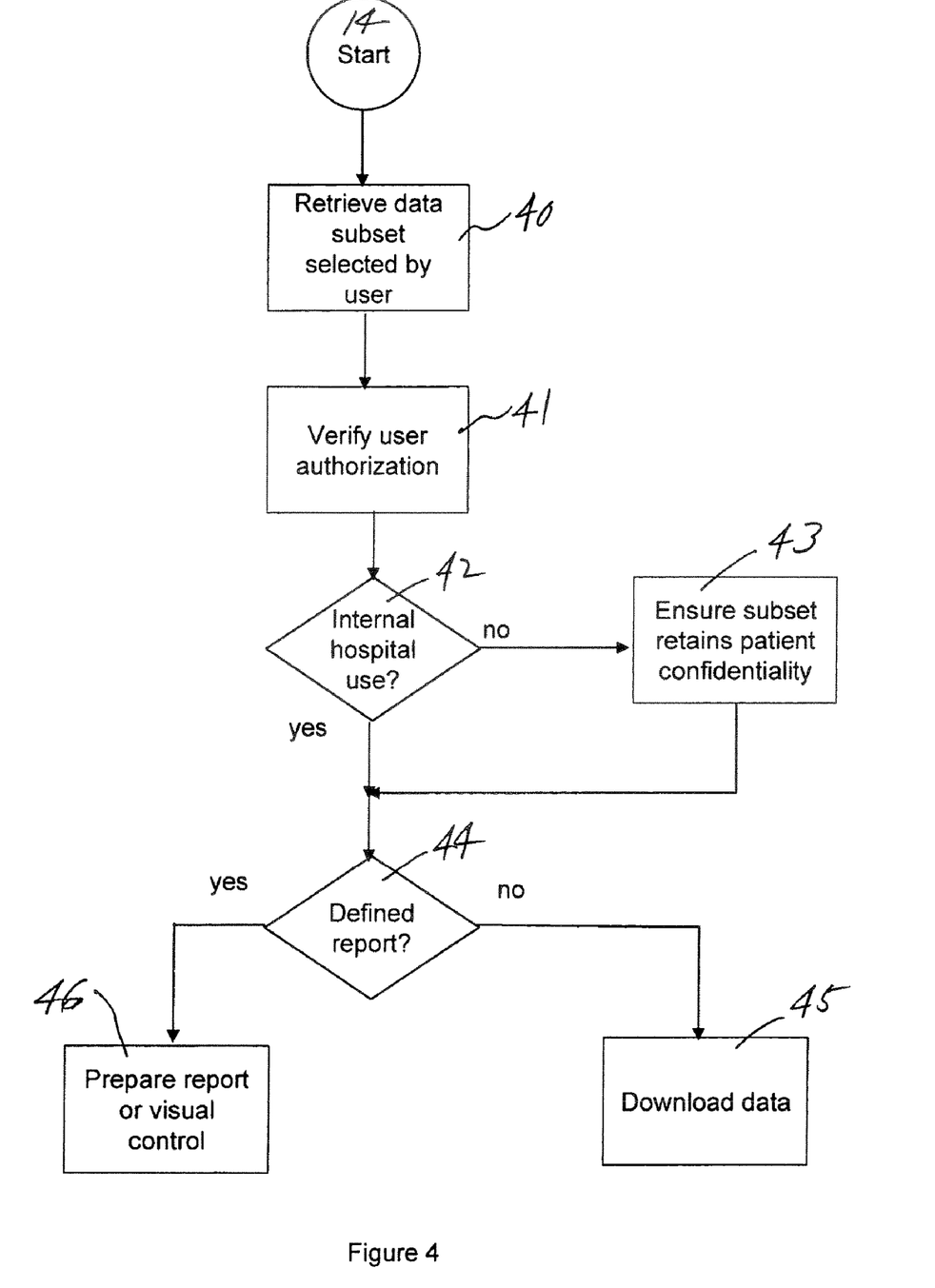
FIG. 4 is flow diagram of the operation of the hospital performance monitoring module shown in FIG. 1.

The Hospital Performance Monitoring module 14 of the system 10 will include the ability to analyze the records of patient visits to capture a picture of the hospitals performance that can be used by hospital administration to continually improve treatment quality and reduce costs. Performance in this context can be viewed from a number of perspectives with a number of different measures. Different measures might reflect treatment quality, financial performance, legal liability costs or the performance of specific medical teams or staffers. It will be the hospital administration's responsibility to decide which measures will be used in for what purposes they will be employed. (See sections "4.2 Performance measures for public consumption" and "4.4 Visual controls".) As shown in FIG. 4, a first step 40 is to retrieve a data subset selected by the user. A next step 41 is to verify user authorization. At a decision point 42, a check is made and the method branches at "no" is the data is not for internal hospital use. A step 43 is performed to ensure that the subset retains patient confidentiality and the method joins a "yes" branch from the decision point 42. At a decision point 44, if a report is not defined, the method branches at "no" and enters a step 45 wherein the data subset is downloaded from the database 11. A defined report causes a branch at "yes" and the method enters a step 46 wherein a report is prepared or a visual control (See Section 4.4) is generated.

4.2 Performance Measures for Public Consumption

The system will capture performance measures similar to existing measures reported in public documents such as the Leapfrog Survey. Such measures could be used to provide credible data that can be used in the hospital's marketing efforts. Thus, the collected data is organized in a step 40 and reports of the various measures are generated in a step 46. These measures might be provided in the form of brochures that are updated quarterly or even in automated displays in public areas that provide real-time information wherein information is published. Hospital administration should have great flexibility in determining what measures to use and how to use them.

4.3 Example

An enormous amount of information is captured by the system. Hospital administration can use this information to provide measures of performance from a number of perspectives. The list below provides some examples but it barely scratches the surface of what is possible.

mortality rates
    average cost per patient stay
    average cost per patient-year for a given population
    number of patients cared for annually per bed
    average annual liability costs per bed
    any of the above broken out by medical specialty, practitioner, diagnosis, medication, surgical procedure, etc.
    vacancy rates 4.4 Visual Controls Many visual controls already exist in a hospital setting. For example, if the ER waiting room is overflowing, is an obvious indicator that the system is not handling the load. The information captured by the TMS system will give hospital administration the ability to create additional visual controls in the step 46. These controls will appear in areas easily accessible by the staff and may or may not be visible to the patients. The intent of these controls is to allow the staff to anticipate problems before they occur. For example, the anticipated queue size for medical imaging equipment based on treatment orders across the hospital might be displayed for relevant staff members. For areas where just-in-time inventory control is not appropriate, inventory levels of critical supplies might be displayed in real-time. Many of these controls will have to be based on hospital size, medical specialty involved or other implementation specific details. The system will provide the flexibility to customize visual controls for specific implementations.

5.0 Healthcare Insurance Billing/Patient Billing

The treatment management system 10 according to the present invention will have the ability to provide automatic, timely and accurate invoices to responsible parties through the Healthcare Insurance Billing module 15 and the Patient Billing module 16. The diagnosis code used to index the treatment regimen data either will be identical to or mapped to the DRG codes used for insurance billing. The system will have knowledge of all supplies, services and facilities used in treating the patient and can therefore bill accordingly. The system will have the capability to support electronic billing or produce printed bills as needed by the responsible party or parties.

6.0 Research & Analysis Support 6.1 Efficacy of Treatment Regimens

For certain types of doctor and hospital services, the consumption of the services is closely correlated to the locally available supply. The use of these supply sensitive services accounts for a major portion of the variation in per capita healthcare cost between geographic regions. Studies have shown that healthcare costs in more expensive regions can be three times that of lower-cost regions. The Dartmouth Atlas Project provides a wealth of information on variations in treatment regimens and costs in different regions of the United States. For more information see "http://www.dartmouthatlas.org". There was no statistically significant variation in quality measures such as mortality rates between regions. In other words, the increased expenditures did not result in any readily apparent improvement in medical quality.

There are also instances where treatment regimens vary because medical science has not advanced sufficiently to show that a particular treatment regimen has a clear advantage. In such cases, doctors must use their own opinions. While this will always be the case, this system 10 captures both the treatment regimens and the associated outcomes with the Research & Analysis Support module 17. This will allow medical researchers to assess aggregate data and compare different treatment regimens for similar diagnoses. Combined with the self learning nature of the system, more effective treatment regimens should emerge much more quickly and be stored in the system. Again, both cost and quality would be impacted. Analysis and publication of the data captured by the treatment monitoring systems should lead to a substantial increase in treatment standardization.

Figure 5:
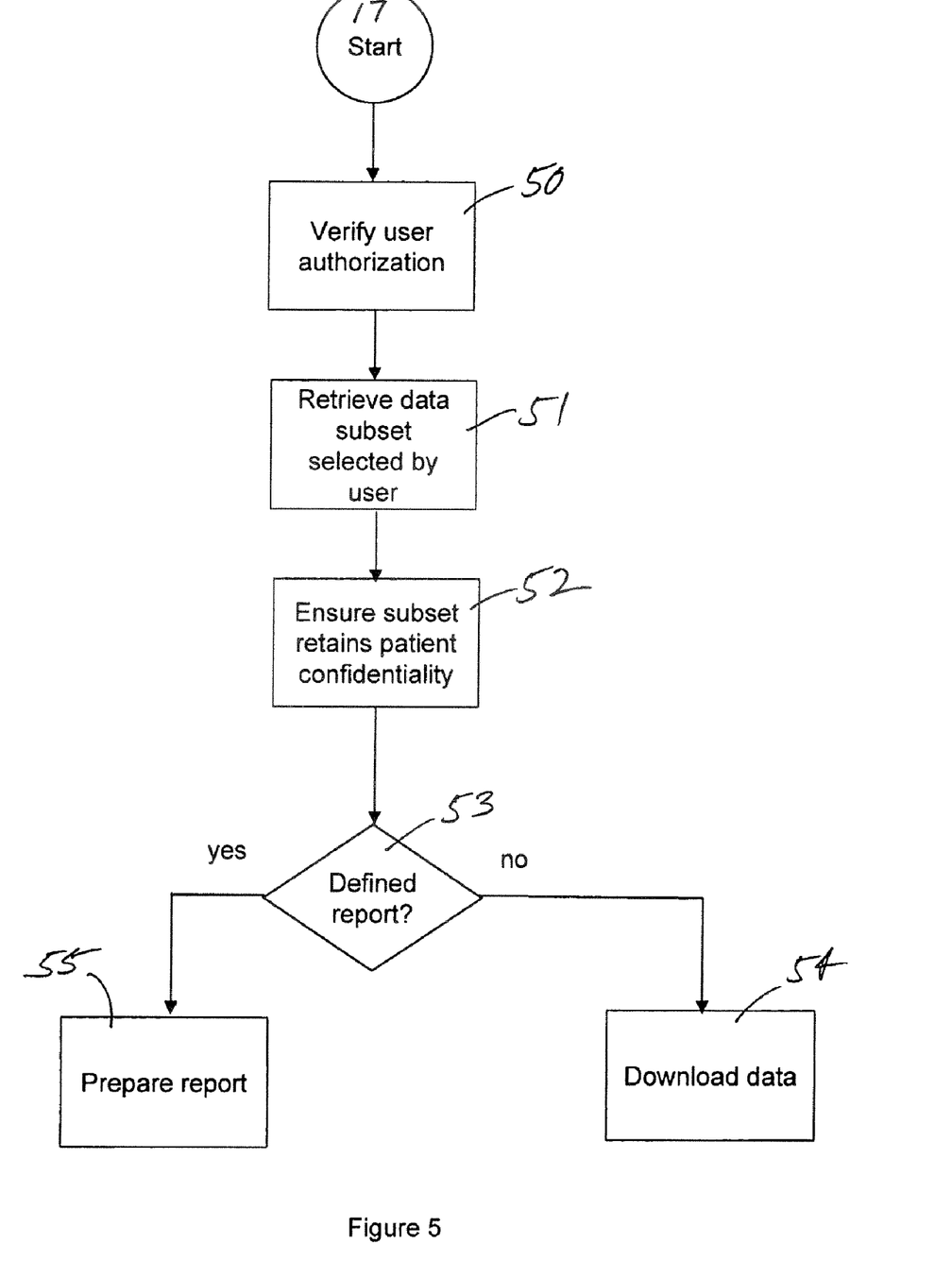
FIG. 5 is flow diagram of the operation of the research and analysis support module shown in FIG. 1.

As shown in FIG. 5, the method starts with a step 50 of verifying user authorization. Next, a data subset selected by the user is retrieved from the database 11 in a step 51. A step 52 ensures that the subset retains patient confidentiality. In a decision point 53, if a report is not defined, the method branches at "no" to a step 54 wherein the data is downloaded. If a report is defined, the method branches at "yes" to a step 55 to prepare the report.

6.2 Impact on Health Care Cost for Specific Patient Populations

The treatment management system 10 will capture sufficient information to estimate the impact of the system itself on the quality and cost of any patient population for which there is a sufficient sample size. This might be based on demographics such as identifying the impact on geriatric patients or children. Health-care insurance providers may wish to compare the cost of healthcare for their customers that use hospitals that have implemented the treatment management system versus those that use hospitals that have not implemented it. Differences in cost and quality across geographic regions could be analyzed. The potential combinations are too numerous to list here.

6.3 Expansion of Hospital Performance Measurement

The cost and quality of health care delivered can be compared across hospitals or groups of hospitals within the same hospital system. A given hospital system might compare the performance of hospitals in different metropolitan areas, geographic regions, etc. If the data were made publicly available, comparisons across hospital systems would be possible.

6.4 Analytical Support Related to Liability

Given the litigious nature of our society, hospitals and physicians will be involved in malpractice litigation no matter how high the quality of the care they provide. Malpractice attorneys tell their clients that the best way to avoid legal difficulties is "document, document, and document!" The system provides very detailed documentation of each patient's treatment. Reporting facilities will be provided for litigation support.

The system 10 will also capture liability expenses related to diagnoses. This information can be used by the hospital administration to document lower liability expenses for their providers of liability insurance. This documentation can be used to justify lower insurance premiums for the hospital.

6.5 Combinations of the Above

The system 10 will provide a very flexible analysis capability. The key limitation on this capability will be to ensure that any subset of the data to be analyzed is of sufficient size to ensure patient confidentiality. This analysis capability can be used to help standardize on the most effective treatment regimens, quickly identify unexpected side effects of new medications and in general, dramatically improving the quality of health care provided to the public.

7.0 Supply Chain Management 7.1 Implementation of Lean Manufacturing Concepts

By capturing information about the current usage of medications and other supplies through the Supply Chain Management module 18, the system 10 will allow much tighter inventory control. The system will use concepts similar to those in lean manufacturing systems to improve quality and eliminate waste. Consumable supplies will be replenished as they are used (in much the same way that kanban systems work in automobile manufacturing). Just-in-time practices will allow hospital inventories to be minimized such that inventories will not substantially exceed levels needed for emergency services.

For this process to work in any facility (manufacturing, medical or otherwise), the facility manager must have the ability to control production to the extent that an even level of output can be produced. For large hospitals most of the activities will approximate this even level of output simply because of the law of large numbers. Unfortunately, for smaller hospitals and for low-volume specialties within larger hospitals, this even level of output would not be dependable. As a result, the system will provide the ability to use a more traditional inventory management approach when JIT methods are not appropriate.

7.2 Inventory-Related Security Issues Such as Management of Controlled Substances By increasing the number of inventory turns, the time required to identify a discrepancy in the inventory levels of any controlled substances would be greatly reduced. Should anyone attempt to steal any of these managed supplies, hospital administration would be quickly alerted to the possibility of theft.

In addition, the use of individual identification at the dose level would allow the source of any defective medications to be quickly identified. This could be implemented through any appropriate technology such as bar-code labels or RFID tags. For example, the system 10 would be able to identify the location of all medications from a defective lot. Any recalled medications could be quickly located and returned to the manufacturer. The same capability could be applied to other supplies of a sensitive nature.

7.3 Improved Support of Purchasing and Accounts Payable Functions

Purchasing at the tactical level will be largely automated. Once appropriate agreements are in place with the suppliers, the system will place orders based on the actual consumption of supplies. (As noted above, more traditional inventory control methods such as calculated economic reorder points can be used where substantial volume fluctuations make JIT inappropriate) Suppliers could be automatically paid on receipt of delivery without waiting for an invoice.

8.0 Personnel Scheduling 8.1 Immediate Detection of Personnel Overload/Imbalance Because each treatment event in a treatment regimen is assigned to a particular role (e.g., nurse, radiologist, etc.), the system has complete knowledge of the short-term requirements for skilled staff. Based on hospital administration supplied parameters, personnel overloads or imbalances in general can be quickly identified using the Personnel Scheduling module 19. Work cells based on medical specialty can be identified and allocated based on expected demand. This technique will facilitate rapid movement of patients through the hospital when appropriate and provide an allocation unit that can be used to react quickly to demand fluctuations.

8.2 Improved Productivity

Using automated medical records and the best available input devices, the time required to complete their responsibilities by hospital staff in general will be reduced. For example, in some hospitals nurses ending their shift must have a significant overlap with the incoming nurse to brief them on the patients that will be under their care. While the function will still be required, the system should dramatically reduce the time required for the briefing.

Physicians entering a treatment regimen that they have used before can do it much more efficiently. Physician productivity will continue to improve as they use the system. The use of work cells based around medical specialties will streamline the treatment of patients after their initial diagnosis. (It may be very appropriate to measure both treatment quality and quantity produced by the medical teams functioning within work cells.)

9.0 TMS Database 9.1 Stored Data Such as:

The TMS database 11 underneath the system will contain a variety of stored information. Some of the major categories that will be captured are as follows:
treatment regimens by diagnosis
treatment plan by patient
patient history
patient billing information
healthcare insurance provider information
hospital employee information
hospital facility information
vendor information 9.2 Event Driven Control Structure In addition to the more common stored information, the system will also capture information about events. This information will be used to drive the control structure operating the treatment process. In general, two types of events will be tracked:

Planned events such as removing a cast or administering the next dose of medication Ad hoc events such as an adverse reaction to the treatment plan.

System actions will be triggered by the occurrence of an event. For most events, an input from a healthcare provider or an automated device will indicate that an event has occurred. The system action triggered by the event may be as simple as recording the event in the patient's history. Depending on the nature of the event, the system might react by notifying a healthcare provider that the patient has had an adverse reaction to the treatment regimen. Planned events have a time based component. When the event is planned, a future time based event is recorded. If the planned event takes place before the associated time based event, the time based event will be deleted. If not, the time based event will serve to notify the system that the planned event did not occur on schedule and the appropriate action should be taken. These planned events will be stored as part of the treatment management system database.

10.0 Implementation Issues 10.1 Architecture

As discussed above, the system 10 will be based on an event driven architecture. It must also be kept in mind that the patient will be mobile. Input devices providing information about the patient or the treatment regimen may be connected to multiple PCs throughout the network. For example, the patient may be taken from their room to use facilities in another part of the hospital. Such facilities might include everything from showers to medical imaging equipment. Monitoring equipment connected to them may move from being wirelessly connected to a PC in a nursing station to being wirelessly connected to a PC in radiology. A radiologist may use that same PC to transfer images to the patient's history. Using technologies such as wireless networks and RFID, the capabilities of the system should move with the patient throughout the hospital. While not required for every implementation, access by remote physicians could be provided via the Internet.

10.2 Security

The system must have very high standards for security and confidentiality. In particular, it must be compliant with HIPPA. This implies that all wireless area connections must be encrypted. Similarly, VPN technology and other emerging technologies should be used to ensure that any Internet access is secure. All devices providing access to the system must have the ability to identify the user of the device biometrically. All inputs to the system must include validation of the user. This validation must be both quick and accurate. Fingerprint readers would be an example of a technology that would be suitable for this purpose. In addition, patient specific information stored in the database must be encrypted.

10.3 Expandability

While initial implementations of the system will be focused on specific hospitals, the architecture and design should facilitate access to patient records across entire hospital systems. This would be expanded to provide access from remote physicians' offices for those physicians associated with the hospital system. Access to a particular patient's information across hospital systems anywhere in the world would be provided in a full implementation.

10.4 Components of the System

Figure 6:
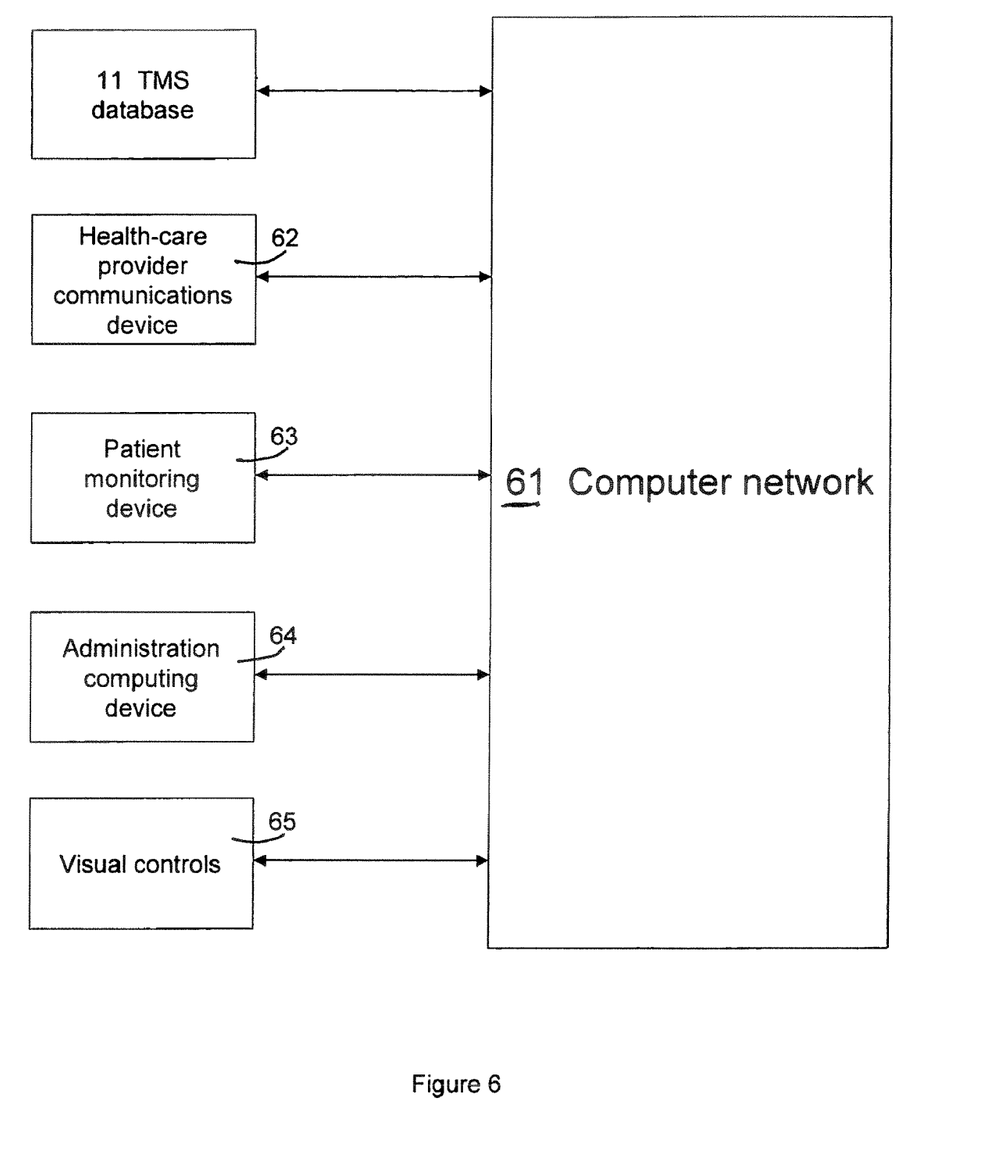
FIG. 6 is a block diagram showing the connections between the components of the treatment management system in accordance with the present invention.

FIG. 6 is a block diagram showing the connections between the components of the treatment management system 10. A network 60 includes the TMS database 11 connected for data exchange with at least one computer 61. The computer 61 runs software that performs all of the data storage and retrieval associated with the database 11 as described above. A healthcare provider terminal 62 represents multiple input/output devices of various types utilized by doctors, nurses, lab technicians, etc. to exchange data with the computer 61. A monitoring device 63 represents various medical devices used in the treatment regimen that exchange data with the computer 61. An administration terminal 64 represents one or more input/output devices of various types utilized by hospital administrators, managers, etc. to exchange data with the computer 61. A visual controls block 65 represents the devices described in Section 4.4 above that exchange data with the computer 61.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A patient treatment management method for a hospital comprising:
   a. providing a computer network comprising at least one healthcare provider terminal, at least one hospital administrator terminal, at least one patient monitoring device, and a computer storing at least one treatment management system database, said treatment management system database storing at least one treatment regimen, said at least one treatment regimen being a modifiable template defining a sequence of treatment events at least one healthcare provider needs to execute in order to treat a diagnosed condition, the at least one treatment regimen further including access permissions for the at least one treatment regimen, and an expected outcome of each treatment event, said expected outcome information further including event success indicators and a customizable alert schedule associated with the success indicators;
   b. accessing the at least one treatment management database by one of the at least one healthcare provider terminal and the hospital administrator terminal and determining at least one decision point in the sequence of treatment events of the at least one treatment regimen and set a default system alert schedule associated with the at least one decision point;
   c. accessing the at least one treatment management database by the at least one healthcare provider terminal and selecting the at least one treatment regimen from the treatment management system database, said selecting responsive to said access permissions for the at least one treatment regimen;
   d. generating at least one patient-specific treatment plan from the selected at least one treatment regimen, wherein said generating includes at least one of accepting the existing treatment regimen, modifying the treatment events responsive to the patient's medical history, adding or removing at least one treatment event, and combining two or more treatment regimens;
   e. customizing the alert schedule responsive to said generating the at least one patient-specific treatment plan, wherein said customizing includes at least one of adding or removing at least one additional treatment event success indicator and an alert schedule associated with the success indicator, and modifying the alert schedule associated with the patient-specific treatment plan;
   f. associating the patient-specific treatment plan with the at least one selected treatment regimen and storing the patient-specific treatment plan in the treatment management system database stored by the computer, wherein said association provides for the identification of the at least one treatment regimen selected in the generation of the patient-specific treatment plan;
   g. monitoring the treatment event outcomes in accordance with the patient-specific treatment plan through at least one of healthcare provider observations received from the at least one healthcare provider terminal and patient data received from the at least one monitoring device;
   h. determining that at least one treatment event outcome success indicator has not been met and issuing an alert in accordance with the customized alert schedule;
   i. determining that the at least one decision point in the sequence of treatment events has been reached;
   j. identifying with the computer the at least one treatment regimen which was used as the modifiable template for the at least one patient-specific treatment plan that is resulting in the at least one treatment event outcome success indicator not being met;
   k. determining a defect in the at least one treatment regimen related to the at least one treatment event outcome success indicator not being met in the at least one treatment plan;
   l. modifying the at least one treatment regimen stored in the treatment management system database to correct for the defect determined in the at least one treatment plan;
   m. storing the modified at least one treatment regimen in the treatment management system database;
   n. identifying all patients currently being treated with a treatment plan based on the treatment regimen that has been determined to be defective; and
   o. generating a notification according to the default system alert schedule to the healthcare providers responsible for the patients currently being treated with a treatment plan based on the defective one of the treatment regimens in the hospital.

2. The method according to claim 1 including providing hospital administrators and healthcare providers with access to the treatment management system database through the computer network to analyze and compare the efficacy of alternative treatment regimens by diagnosis.

3. The method according to claim 2 including accessing the treatment management system database through the computer network to determine an efficacy under varying conditions involving factors, the factors including at least one of patient characteristics, prior medical history and treatment delivery providers.

4. The method according to claim 1 including generating from the computer network a notification to the healthcare providers responsible for the patients currently being treated with a treatment plan based on the defective one of the treatment regimens in hospitals other than the hospital.

5. The method according to claim 1 wherein said steps c. to e. include a physician modifying an existing treatment regimen stored in the treatment management system database to create the at least one treatment plan and assigning the at least one treatment plan to the patient.

6. The method according to claim 1 wherein said steps c. to e. include a physician modifying an existing treatment regimen stored in the treatment management system database to generate the at least treatment plan either as an improved replacement for the existing treatment regimen or as an alternative treatment regimen for the existing treatment regimen.

7. A patient treatment management system for a hospital comprising:

at least one healthcare provider terminal;

at least one hospital administrator terminal;

at least one patient monitoring device; and a computer storing at least one treatment management system database and connected with the at least one healthcare provider terminal, the at least one hospital administrator terminal, and the at least one patient monitoring device to form a computer network, said treatment management system database storing at least one treatment regimen, said at least one treatment regimen being a modifiable template defining a sequence of treatment events at least one healthcare provider needs to execute in order to treat a diagnosed condition, the at least one treatment regimen further including access permissions for the at least one treatment regimen, and an expected outcome of each treatment event, said expected outcome information further including event success indicators and a customizable alert schedule associated with the success indicators, wherein the computer further includes at least one of a treatment planning module and a treatment monitoring module, the computer permitting the healthcare provider to access the at least one treatment management database on one of the at least one healthcare provider terminal and the hospital administrator terminal using the treatment planning module and determine at least one decision point in the sequence of treatment events of the at least one treatment regimen and set a default system alert schedule associated with the at least one decision point, access the at least one treatment management database on the at least one healthcare provider terminal using the treatment planning module and select the at least one treatment regimen from the treatment management system database, said selecting responsive to said access permissions for the at least one treatment regimen, generate at least one patient-specific treatment plan from the selected at least one treatment regimen on the at least one healthcare provider terminal using the treatment planning module, wherein said generating includes at least one of accepting the existing treatment regimen, modifying the treatment events responsive to the patient's medical history, adding or removing at least one treatment event, and combining two or more treatment regimens, create the alert schedule responsive to said generating the at least one patient-specific treatment plan on one of the at least one healthcare provider terminal and the at least one hospital administrator terminal using the treatment planning module, wherein said creating includes at least one of selecting the at least one existing customizable alert schedule associated with the at least one treatment regimen from which the at least one patient-specific treatment plan is generated, adding or removing at least one additional treatment event success indicator and an alert schedule associated with the success indicator, and modifying the alert schedule associated with the at least one patient-treatment plan, associate the patient-specific treatment plan with the at least one selected treatment regimen and store the patient-specific treatment plan in the treatment management system database stored on the computer, wherein said association provides for the identification of the at least one treatment regimen selected in the generation of the patient-specific treatment plan, monitor the treatment event outcomes using the treatment monitoring module in accordance with the patient-specific treatment plan through at least one of healthcare provider observations received from the at least one healthcare provider terminal and patient data received from the at least one monitoring device, determine that at least one treatment event outcome success indicator has not been met using the treatment monitoring module and issue an alert in accordance with the customized alert schedule, determine that the at least one decision point in the sequence of treatment events has been reached using the treatment monitoring module, identify with the computer the at least one treatment regimen which was used as the modifiable template for the at least one patient-specific treatment plan that is resulting in the at least one treatment event outcome success indicator not being met, determine a defect in the at least one treatment regimen related to the at least one treatment event outcome success indicator not being met in the at least one treatment plan using the treatment monitoring module, modify the at least one treatment regimen stored in the treatment management system database to correct for the defect determined in the at least one treatment plan, store the modified at least one treatment regimen in the treatment management system database, identify all patients currently being treated with a treatment plan based on the treatment regimen that has been determined to be defective, and generate a notification according to the default system alert schedule to the healthcare providers responsible for the patients currently being treated with a treatment plan based on the defective one of the treatment regimens in the hospital.

8. The system according to claim 7, wherein said computer further includes a hospital monitoring module, a healthcare insurance billing module, a patient billing module, a research and analysis support module, a supply chain management module and a personnel scheduling module.

9. The system according to claim 7, wherein said computer permits hospital administrators and healthcare providers to analyze and compare the efficacy of alternative said treatment regimens by diagnosis.

10. The system according to claim 9 wherein said computer permits the at least one healthcare provider to determine the efficacy under varying conditions involving factors, the factors including at least one of patient characteristics, prior medical history and treatment delivery providers that have been stored in said at least one database.

11. The system according to claim 7, wherein said computer generates a notification to the healthcare providers responsible for the patients currently being treated with a treatment plan based on a defective one of the treatment regimens in hospitals other than the hospital.

12. The system according to claim 7, wherein said computer uses said at least one database to evaluate hospital performance with respect to cost and patient outcomes by a variety of factors, the factors including at least one of patient demographics including geographic variations and health care insurance providers.

13. The system according to claim 7, wherein said computer said at least one database to prepare bills for patients and their insurance providers.

14. The system according to claim 7, wherein said computer uses said at least one database to assist researchers in the analysis of treatment efficacy, side effects of new medications, alternative treatment regimen selection criteria and in general, facilitate the propagation of evidence based medicine.

15. The system according to claim 7, wherein said computer identifies supply usage, verifying a proper usage of controlled substances and other supplies and placing orders to replenish supplies consistent with lean manufacturing and supply chain management techniques.

16. The system according to claim 7, wherein said computer identifies personnel staffing requirements based on planned events from existing said treatment plans and historical admission rates.

* * * * *

UNITED STATES PATENT AND TRADEMARK OFFICE
CERTIFICATE OF CORRECTION

PATENT NO.        : 7,765,114 B2
APPLICATION NO. : 11/947357
DATED             : July 27, 2010
INVENTOR(S)       : W. Vaughn Frick It is certified that error appears in the above-identified patent and that said Letters Patent is hereby corrected as shown below:

In Specification:
Under DESCRIPTION OF THE PREFERRED EMBODIMENT, paragraph 3.2:
column 7, line 37 -- "the patient question" should read "the patient in question"

Under DESCRIPTION OF THE PREFERRED EMBODIMENT, paragraph 4.1:
column 8, line 37 -- "which measures will be used in for what purposes" should read "which measures will be used and for what purposes"

Under DESCRIPTION OF THE PREFERRED EMBODIMENT, paragraph 10.2:
column 13, line 7 -- "HIPPA" should read "HIPAA"

Under the Claims, Claim 7:
column 16, line 24 -- there should be a paragraph break after the phrase "one patient-treatment plan," and the phrase "associate the patient-specific" should start the new paragraph Signed and Sealed this Fifth Day of October, 2010

David J. Kappos
*Director of the United States Patent and Trademark Office*